United States Patent [19]

Hely

[11] Patent Number: 5,067,486

[45] Date of Patent: Nov. 26, 1991

[54] ANKLE STABILIZING APPLIANCE

[75] Inventor: John P. Hely, Charlotte, N.C.

[73] Assignee: Medical Specialties, Inc., Charlotte, N.C.

[21] Appl. No.: 500,607

[22] Filed: Mar. 28, 1990

[51] Int. Cl.$^5$ .............................................. A61F 5/00
[52] U.S. Cl. .............................. 128/80 H; 128/80 R; 128/166
[58] Field of Search ..................... 128/80 R, 80 H, 166

[56] References Cited

U.S. PATENT DOCUMENTS

| | | | |
|---|---|---|---|
| 3,073,305 | 1/1963 | Biggs, Jr. et al. | 128/80 H |
| 3,506,000 | 4/1970 | Baker. | |
| 3,573,482 | 3/1986 | Williams, Jr. | 128/80 R |
| 4,280,488 | 7/1981 | Polsky et al. | 128/80 H |
| 4,313,433 | 2/1982 | Cramer. | |
| 4,323,058 | 4/1982 | Detty. | |
| 4,597,395 | 7/1986 | Barlow et al. | |
| 4,621,648 | 11/1986 | Ivany | 128/80 H |
| 4,729,370 | 3/1988 | Kallassy. | |
| 4,844,058 | 7/1989 | Vogelbach. | |
| 4,878,504 | 11/1989 | Nelson | 128/80 H |

FOREIGN PATENT DOCUMENTS 3416253 11/1985 Fed. Rep. of Germany ...... 128/166

OTHER PUBLICATIONS

"The Matrix Ankle Support", Matrix Medical Corp., 1 page.
"The TRU-FIT Ankle Support", TRU-FIT Marketing Corp., 1 page.
"The PRO Super 8 Ankle Brace", Pro Orthopedic Devices, 1 page.
"SportSplint ®-AA-11 Vinyl", Orthopedic Technology Inc., 1 page.
"PRO Introduces The All New J. L. Ankle Brace", PRO TM, 1 page.
"3D TM 3-Way Functional Ankle Brace—The One That Does It All", 3D TM Orthopedic Inc., 1 page.

Primary Examiner—Robert Bahr
Assistant Examiner—Linda C. M. Dvorak
Attorney, Agent, or Firm—Bell, Seltzer, Park & Gibson

[57] ABSTRACT

An ankle stabilizing appliance is disclosed which comprises a boot-like body member, and a pair of stabilizing straps which extend in opposite directions from the rear edge portion of the body member. Each of the stabilizing straps is adapted to extend across and under the foot of the wearer, and then upwardly to a releasable attachment point on the side of the body member. The body member also includes a pair of oppositely directed binding straps which overlie the stabilizing straps and which are adapted to be looped about the ankle of the wearer.

10 Claims, 3 Drawing Sheets

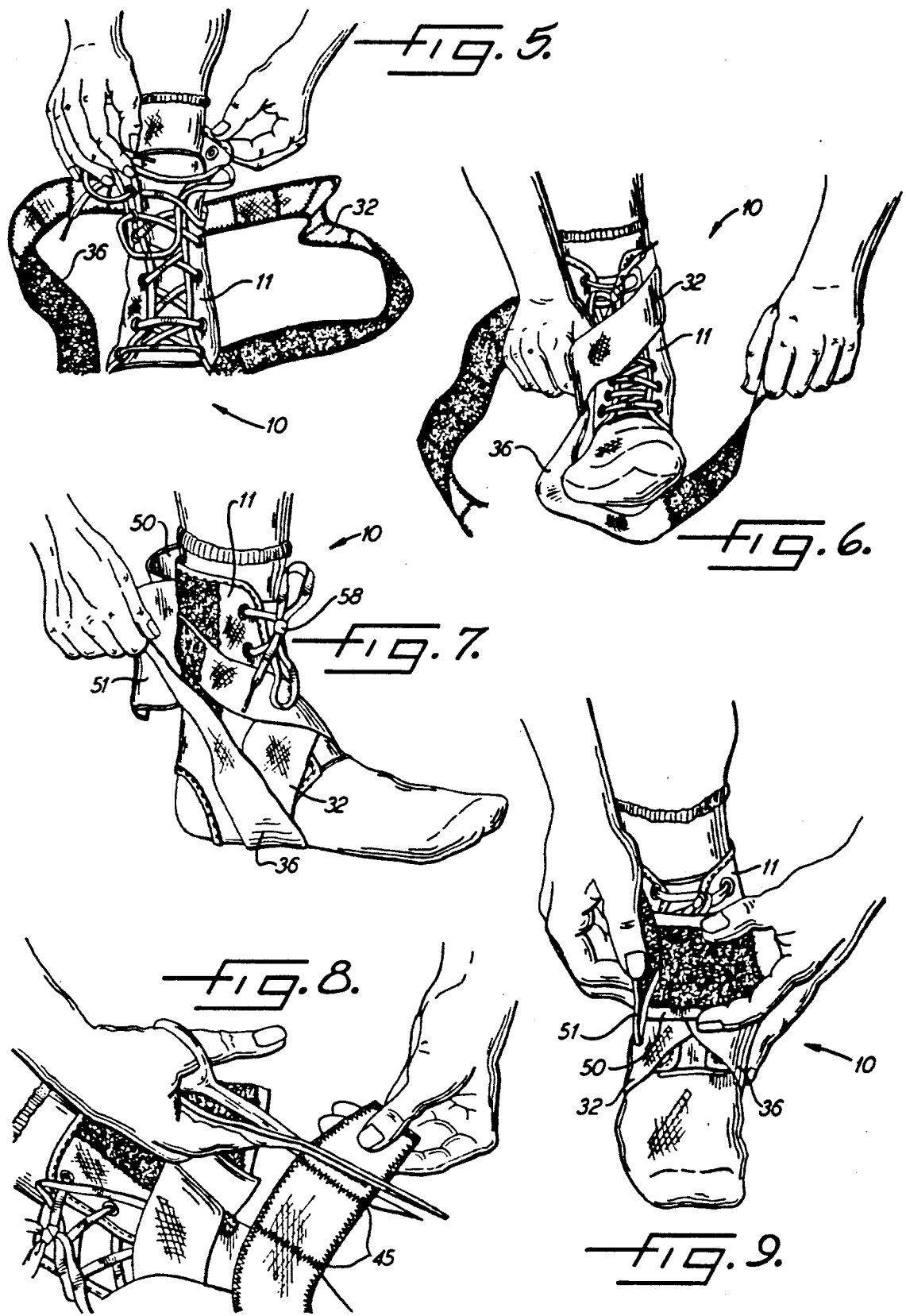

ANKLE STABILIZING APPLIANCE

FIELD OF THE INVENTION

The present invention relates to an ankle stabilizing appliance which is designed to prevent injuries to the ankle during strenuous physical activity.

BACKGROUND OF THE INVENTION

Athletes as well as others who engage in physical activity expose themselves to the possibility of various types of ankle injuries including sprains. A majority of coaches, trainers, and athletes agree that some type of ankle support during physical exertion is desirable, and the traditional form of support is ankle taping. However, ankle taping usually acts to reduce the range of ankle motion, which may restrict performance. Additionally, taping may result in diminished muscle tone and possible atrophy of ankle supporting muscles due to lack of conditioning through disuse. Finally, the benefit of taping for ankle support often lasts in duration for only a relatively short time, since the taping can be loosened during exercise. There are numerous other disadvantages associated with taping which make the use of some other form of ankle support a desirable alternative.

Various types of non-taping ankle supporting devices have also been proposed. These prior devices include various designs having boot-like members which fit over the foot and ankle portion of the athlete as well as strapping devices attached to the boot for wrapping the ankle. However, these known devices also become loose during use, and it is difficult to re-tighten the devices while on the foot. Also, it is believed that none of the prior art devices of this type effectively prevents both inversion and eversion of the ankle, while permitting flexion and dorsiflexion of the foot. More particularly, the prevention of inversion and eversion is desirable to prevent spraining of the ankle, while flexion and dorsiflexion are necessary to permit full athletic activity.

It is accordingly an object of the present invention to provide an ankle stabilizing appliance which overcomes the above noted disadvantages and limitations associated with ankle taping and the prior ankle stabilizing supports.

It is also an object of the invention to provide an ankle stabilizing appliance which may be easily applied by the athlete while offering substantial ankle support, and which is comfortable in use.

It is another object of the present invention to provide an ankle stabilizing appliance which provides significant ankle support over an extended period of time, and which can be readily re-tightened while the device is on the foot.

It is yet another object of the invention to provide an ankle stabilizing appliance which prevents both inversion and eversion of the ankle, while permitting flexion and dorsiflexion.

SUMMARY OF THE INVENTION

The above and other objects and advantages are achieved in accordance with the present invention by the provision of an ankle stabilizing appliance which comprises a boot-like body member formed of flexible non-elastic material and which is adapted for receiving the ankle and rear foot portion of the athlete. The body member has an ankle portion adapted to overlie the sides and rear of the ankle of the wearer and it has a length which is sufficient to extend above the malleoli of the wearer. The foot portion of the body member extends under the foot of the wearer. The body member also includes opposing laterally spaced apart front edges extending along the full length of the ankle portion and the foot portion.

The ankle portion of the body member defines an inside panel on one side of the ankle and an outside panel on the opposite side of the ankle. The ankle portion also defines a rear edge portion which extends vertically between the inside and outside panels and thus along the Achilles tendon of the wearer. Interconnection means, such as lacing, is provided for drawing the front edges of the body member together so as to permit the body member to be tightly secured about the ankle and rear portion of the foot of the wearer.

Additionally, the appliance includes a pair of elongate non-elastic stabilizing straps which are each fixed at one end thereof to the rear edge portion of the ankle portion. The straps extend laterally in opposite directions from the rear edge portion, and one strap defines an inside strap extending from the rear edge portion toward the inside panel and the second strap defines an outside strap extending from the rear edge portion toward the outside panel. Pressure sensitive releasable closure means is attached to the inside panel of the ankle portion as well as to the free end of the inside strap. Additionally, pressure sensitive releasable closure means is attached to the outside panel of the ankle portion and the free end of the outside strap.

In use, the inside strap is brought across the inside panel of the ankle portion, over the top of the wearer's foot, downwardly across the outside of the wearer's foot, under the wearer's foot, and then upwardly so that the free end thereof can be attached to the inside panel of the ankle portion of the body member. The outside strap is brought across the outside panel of the ankle portion, over top of the wearer's foot, downwardly across the inside of the wearer's foot, under the wearer's foot, and then upwardly so that the free end of the outside strap can be attached to the outside panel of the ankle portion of the body member.

In the preferred embodiment, the stabilizing straps are attached to the rear edge portion of the ankle portion at an elevation above the malleoli of the wearer, to provide desirable leverage for effectively restraining inversion and eversion of the ankle, while permitting dorsiflexion. Also, the appliance preferably includes a pair of binding straps which are each fixed at a first end to the ankle portion at the rear edge portion and so as to overlie the stabilizing straps. The opposite free ends of the binding straps extend laterally in opposite directions, and pressure sensitive closure means is attached to each free end so that the binding straps are adapted to be looped about the ankle of the wearer and interconnected to each other so as to overlie portions of the stabilizing straps and the lacing.

An important feature of the invention is the fact that the appliance is adapted to be readily re-tightened while on the wearer's foot, without requiring that the laces be loosened and then re-tightened. More particularly, the appliance may be re-tightened by releasing the outer binding straps, releasing the two stabilizing straps, pulling up on the free ends of the two stabilizing straps, and then reconnecting the stabilizing straps and binding straps.

BRIEF DESCRIPTION OF THE DRAWINGS

Some of the objects and advantages of the present invention having been stated, others will appear as the description proceeds, when taken in conjunction with the accompanying drawings, in which:

FIGS. 5–9 are perspective views illustrating the steps involved in applying the appliance onto the ankle.

DESCRIPTION OF THE PREFERRED EMBODIMENT

Figure 1:
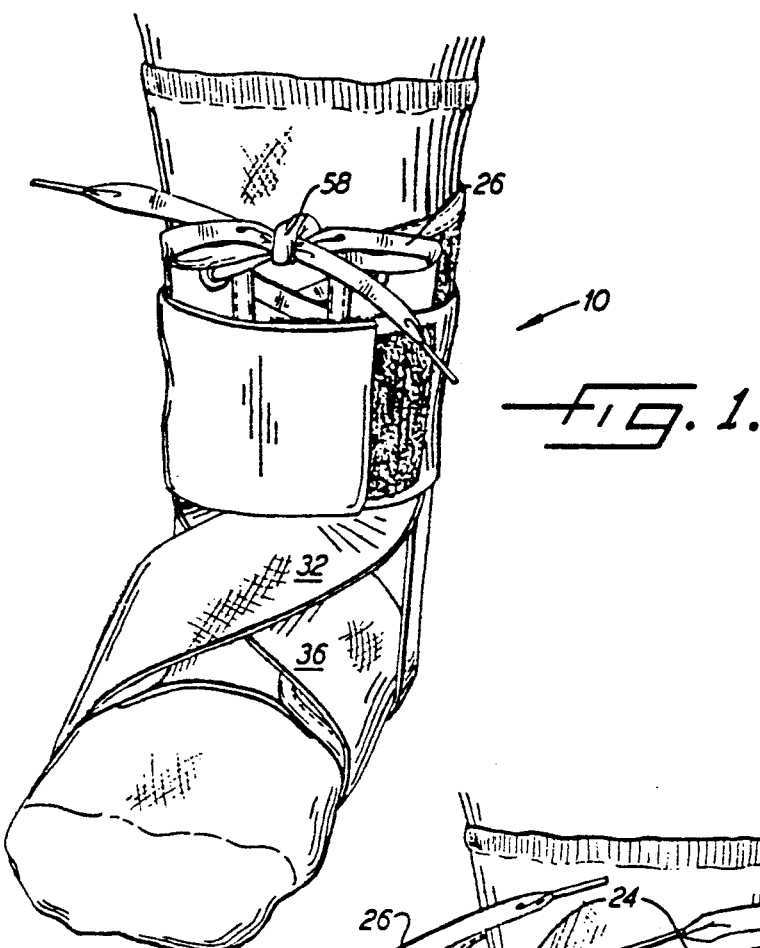
FIG. 1 is a perspective view of an ankle stabilizing appliance which embodies the features of the present invention, shown in operative position on the ankle of a wearer.

The ankle stabilizing appliance of the present invention, and which is also known as an orthosis, is indicated generally at 10 in the drawings. As illustrated, the appliance 10 is designed to be worn over an athletic sock, although an underlying sock is not required. Also, the appliance 10 is designed so as to be capable of being placed on either foot of the wearer and still maintain a high level of support.

The appliance 10 comprises a boot-like body member 11 which is fabricated from a single sheet of flexible non-elastic fabric material. In a preferred embodiment, the non-elastic fabric material is a ballistic nylon fabric which provides a high degree of strength while being light in weight. The sheet of fabric material is folded upwardly into a generally U-shaped configuration when viewed from the front, to define an upper ankle portion 12 which adapted to overlie both sides and the rear of the ankle of the Wearer, and a lower foot portion 14 adapted to extend under the foot of the wear. More particularly, the ankle portion 12 comprises upstanding inside and outside panels 16 and 17 respectively, Which are joined along a vertical seam 18 (FIG. 4), and the foot portion 14 is disposed between the lower ends of the upstanding panels 16 and 17. Also, the ankle portion 12 is of sufficient length so as to extend vertically above the malleoli of the wearer. A cutout 20 is formed at the bottom of the ankle portion 12 and the rear of the foot portion 14 of the body member, for receiving the heel portion of the wearer's foot.

The two upstanding panels 16, 17 of the folded sheet of fabric material also define opposing laterally spaced apart front edges 21, 22 respectively, which extend along the full length of the front of the ankle portion 12 and the foot portion 14. These front edges 21, 22 are curved in nature so that when in place, the body member 11 conforms to the front of the shin and the top of the foot of the wearer.

An overedge binding strip 24 is sewn along the front edges 21, 22, as well as along the edges which define the heel opening 20, the top of the panels 16, 17, and the front of the foot portion 14. Also, a plurality of metal eyelets 25 are placed along the length of each of the opposing front edges 21, 22, and a flexible strand of lacing 26 is threaded through the eyelets to interconnect the edges 21, 22 and permit the edges to be drawn toward each other in the conventional manner, and thereby cause the body member to be tightly secured about the ankle and rear portion of the foot of the wearer.

Figure 4:
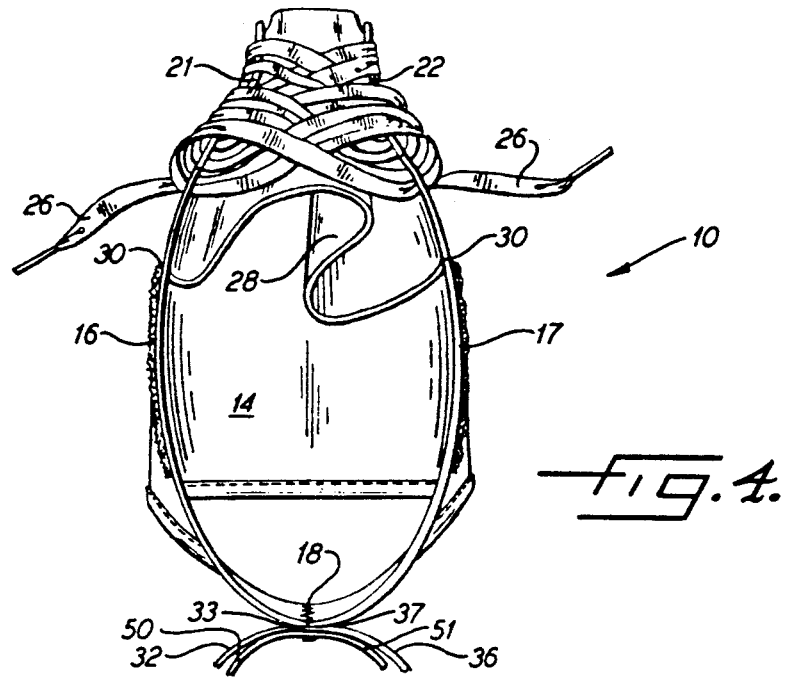
FIG. 4 is a top plan view of the appliance.

A tongue 28 as best seen in FIG. 4 is secured between the opposing laterally spaced apart front edges 21, 22 of the body member. The vertical edges of the tongue 28 are attached to the inside surfaces of the inside and outside panels 16, 17 of the body member along a seam line 30. The tongue 28 is composed of an elastic fabric material, such as a high temperature stretch nylon fabric, and it serves to facilitate the application of the appliance, and to provide additional padding.

Figure 3:
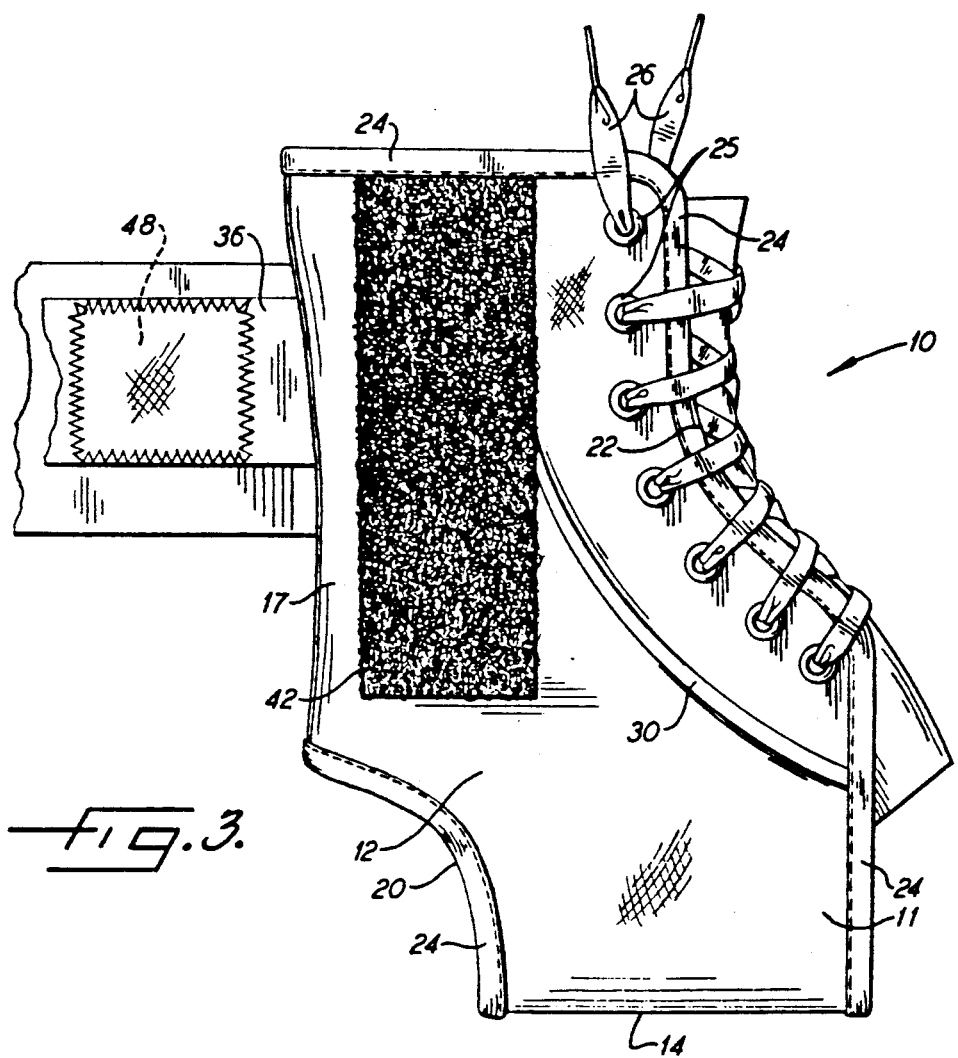
FIG. 3 is a side elevation view of the appliance.

The body member 11 also defines a rear edge portion which extends vertically along the rear of the ankle portion 12 at the seam line 18 between the inside panel 16 and the outside panel 17. This rear edge portion therefore extends along the Achilles tendon of the wearer. As best seen in FIGS. 3 and 4, the rear edge portion is arcuately curved in an inward direction along the vertical length and so as to closely conform to the anatomy of the posterior portion of the wearer's foot.

A pair of elongate non-elastic straps 32, 36 are attached to the body member, with each strap comprising a first end fixed to the ankle portion along the seam line 18 at the rear edge portion, and an opposite free end. More particularly, the strap 32 has a fixed first end 33 and a free opposite end 34, and the strap 36 has a fixed first end 37 and an opposite free end 38. The straps 32, 36 are attached to the rear edge portion at an elevation which is designed to be located above the malleoli of the wearer. Also, the straps 32, 36 extend laterally in opposite directions and so that the strap 32 defines an inside strap extending from the rear edge portion toward the inside panel 16, and the strap 36 defines an outside strap extending from the rear edge portion toward the outside panel 17. The straps 32, 36 are preferably composed of a ballistic nylon fabric so as to provide superior strength in a relatively thin cross section.

For the purpose of securing the inside stabilizing strap 32 about the foot of the wearer in the manner described below, there is provided a first pressure sensitive closure means, which comprises two cooperating strips of fabric 40, 41, with the one strip 40 being attached to the outer face of the inside panel 16 and the other strip 41 being attached to the free end 34 of the strap 32. Also, a second releasable closure means is provided which comprises a third strip of fabric 42 attached to the outside panel 17 and a fourth strip of fabric 43 attached to the free end 38 of the strap 36. In a preferred embodiment, the two strips which form each of the releasable closure means are in the form of hook-like filaments and loop-like filaments respectively, of the type commonly sold under the trademark VELCRO.

Figure 2:
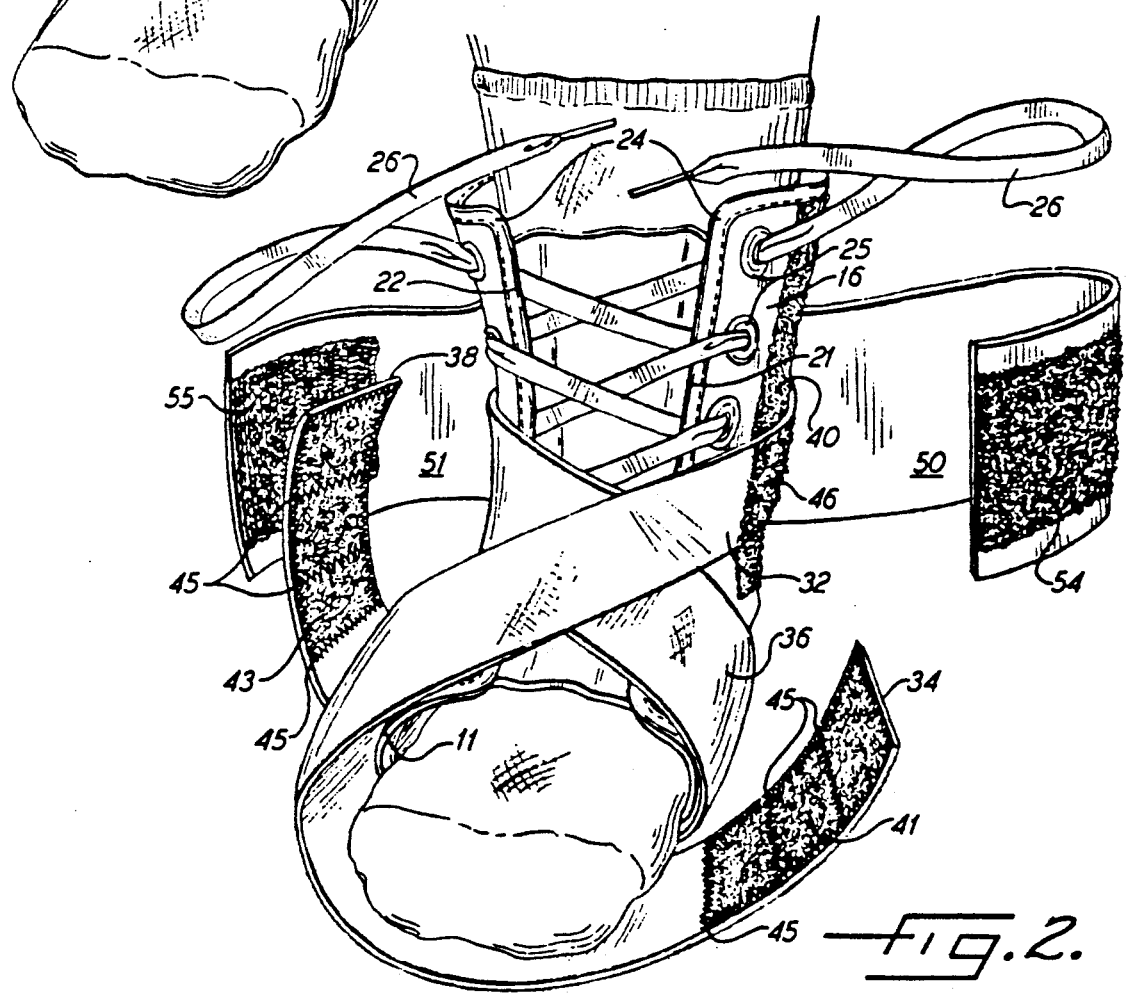
FIG. 2 is an exploded view of the appliance on the ankle of a wearer.

The strips 40, 42 which are attached to the inside and outside panels of the body member respectively, extend vertically from a location near the wearer's ankle, i.e. the bottom of the ankle portion, to the top of the ankle portion. The strips 41, 43 which are attached to the free ends of the straps 32, 36 respectively, are elongate as best seen in FIG. 2, and include intermediate transverse seam lines 45 which permit the straps to be shortened by cutting along the outside of one of the seam lines in the manner shown in FIG. 8. The transverse seam line 45 which is closest to the cut will insure the attachment of the strip to the free end after such cutting.

An additional fabric strip 46 is attached to the outside of the inner stabilizing strap 32 at a location near the fixed end 33 of the strap. This strip 46 is of the same type, either loop or hook, as strip 40, and it is located in such a position that when in use, the additional strip 46 overlies the strip 40. A similar strip 48 is attached to the outside of the outer strap 36 for engaging the strip 43 at the end of such strap.

A pair of binding straps 50, 51 are provided, which are adapted to be looped about the ankle of the wearer so as to overlie portions of the stabilizing straps 32, 36 and the lacing 26 and eyelets 25. More particularly, the binding straps 50, 51 each have a first end fixed to the rear edge portion of the ankle portion, and an opposite free end. The straps 50, 51 thus extend laterally in opposite directions from the rear edge portion and the straps 50, 51 overlie the stabilizing straps 32, 36. The free ends of the binding straps 50, 51 mount a releasable closure means in the form of a pressure sensitive closure means which comprises a loop-type filament strip 54 and a hook-type filament strip 55. In the preferred embodiment, the binding straps 50, 51 are composed of an elastic fabric. The strip 54 is attached to the outside surface of the binding strap 50 at or near the free end, and the second strip 55 is attached to the inside surface of the other binding strap 51 at or near the free end.

As illustrated in FIGS. 5-9, the boot-like body member 11 is adapted to be placed on either of the wearer's feet, preferably over top of an athletic sock. Once on the foot, the lacing 26 is drawn tight, and the two free ends are tied together to form a knot as illustrated at 58 in FIG. 7.

The stabilizing straps 32, 36 are then wrapped around the foot as depicted in FIGS. 6 and 7. The first strap to be applied can be either the inside strap 32 or the outside strap 36. For purposes of illustration, the first strap to be applied will be the inside strap 32, which is brought across the inside panel 16 of the ankle portion of the body member and over top of the lacing 26 extending up the opposing front edges of the body member on the wearer's foot. The inside strap 32 is then extended downwardly across the outside of the wearer's foot, i.e. across the outside surface of the foot portion and under the wearer's foot. Finally, the inside strap 32 is extended upwardly to the inside panel 16 so that the strip 41 on the free end can be releasably attached to the strip 40 on the inside panel of the ankle portion of the body member.

The additional strip 46 on the inner end portion of the strap 32 provides an additional attachment point for the strip 41 on the free end of the strap, to thereby assure that the free end is securely fixed in place.

The second stabilizing strap, which in the illustrated embodiment comprises the outside strap 36, is then wrapped around the foot by first bringing it across the outside panel 17 and over the top of the lacing 26. The strap 36 is then extended downwardly across the inside of the wearer's foot, i.e across the ankle portion of the body member, and under the wearer's foot. Finally, the strap is extended upwardly past the foot portion so that the free end 38 can be releasably attached to the outside panel of the ankle portion of the body member by means of the strips 42, 43 of the second closure means.

As previously discussed, the stabilizing straps 32, 36 are of sufficient length to allow complete wrapping of the foot in accordance with the above described procedure. Also, the straps 32, 36 are adjustable in length by cutting the strap at a point immediately beyond one of the seam lines 45. As depicted in FIG. 8, scissors may be used to cut the straps at the point just beyond the seam line.

To complete the application procedure, the binding straps 50, 51 are stretched and engaged in place. More particularly, the first binding strap 50 is stretched across the front of the body member, and the other binding strap 51 is stretched across the front of the body member in the opposite direction of the first binding strap. The second binding strap 51 is then pressed against the first binding strap so that the mating strips 54, 55 form a pressure sensitive releasable closure. These binding straps 50, 51 thus loop about the ankle of the wearer and overlie portions of the stabilizing straps 32, 36 and the lacing knot 58. The straps 50, 51 thus assist in preventing the stabilizing straps 32, 36 from moving.

The fact that the stabilizing straps 32, 36 are attached to the rear edge portion at an elevation above the malleoli of the wearer, is seen to provide desirable leverage for effectively restraining inversion and eversion of the ankle, while permitting both flexion and dorsiflexion of the wearer's foot. As a further important feature of the appliance, it will be understood that the appliance is adapted to be readily re-tightened while on the wearer's foot, by releasing the outer binding straps 50, 51 and pulling up on the free ends of the two stabilizing straps 32, 36. The appliance also avoids the secondary skin problems commonly associated with taping, including skin sensitivity, blisters, and tape cuts.

Although a preferred embodiment of the invention has been disclosed for illustrative purposes, it is not limited to the specific forms or arrangement of parts herein described and shown. The invention is encompassed within the claims provided hereinafter.

That which we claim is:

1. An ankle stabilizing appliance adapted to provide protection against lateral ankle sprain during participation in sports activities, and comprising
   a boot-like body member of flexible non-elastic material and adapted to receive the ankle and the rear foot portion of the wearer therein, said body member comprising an ankle portion adapted to overlie the sides and rear of the ankle of the wearer and having a length sufficient to extend above the malleoli of the wearer, a foot portion adapted to extend under the foot of the wearer, and opposing laterally spaced apart front edges extending along the full length of said ankle portion and said foot portion, and with said ankle portion defining an inside panel on one side of the ankle, an outside panel on the other side of the ankle, and a rear edge portion which extends vertically between the inside and outside panels and thus along the Achilles tendon of the wearer,
   interconnection means for drawing said front edges of said body member toward each other so as to permit said body member to be tightly secured about the ankle and rear portion of the foot of the wearer,
   a pair of elongate non-elastic stabilizing straps, with said straps each having a first end fixed to said ankle portion at said rear edge portion thereof and at an elevation so as to be located above the malleoli of the wearer, and an opposite free end, and with said straps extending laterally in opposite directions and so as to define an inside strap extending from said rear edge portion toward said inside panel and an outside strap extending from said rear edge portion toward said outside panel,
   first pressure sensitive releasable closure means attached to said inside panel of said ankle portion and to said free end of said inside strap, and second pressure sensitive releasable closure means attached to said outside panel of said ankle portion and to said free end of said outside strap, a pair of binding straps, with said binding straps each having a first end fixed to said ankle portion at said rear edge portion thereof at an elevation corresponding to that of said stabilizing straps, and an opposite free end, and with said binding straps extending laterally in opposite directions and overlying said stabilizing straps, and pressure sensitive closure means attached to said free ends of said binding straps, whereby said inside strap may be brought across said inside panel of said ankle portion, over the top of the wearer's foot, downwardly across the outside of the wearer's foot, under the wearer's foot, and then upwardly and so that said free end thereof may be releasably attached to said inside panel of said ankle portion, and whereby said outside strap may be brought across said outside panel of said ankle portion, over the top of the wearer's foot, downwardly across the inside of the wearer's foot, under the wearer's foot, and then upwardly and so that said free end thereof may be releasably attached to said outside panel of said ankle portion, and such that said binding straps are adapted to be looped about the ankle of the wearer and interconnected to each other and so as to overlie portions of said stabilizing straps and said interconnection means.

2. The ankle stabilizing appliance as defined in claim 1 wherein said binding straps comprise an elastic fabric material.

3. The ankle stabilizing appliance as defined in claim 1 further comprising a tongue of elastic fabric material secured between said front edges of said body member and extending along at least substantially the entire length thereof.

4. The ankle stabilizing appliance as defined in claim 3 wherein said first pressure sensitive releasable closure means comprises a first strip of fabric material composed of hook-like filaments and a second strip of fabric material composed of loop-like filaments, with one of said first and second strips being attached to said inside panel of said ankle portion and the other of said strips being attached to said free end of said inside strap, and said second pressure sensitive releasable closure means comprises a third strip of fabric material composed of hook-like filaments and a fourth strip of fabric material composed of loop-like filaments, with one of said third and fourth strips being attached to the outside panel of said ankle portion and the other of said third and fourth strips being attached to said free end of said outside strap.

5. The ankle stabilizing appliance as defined in claim 4 wherein said inside strap further mounts an additional strip of fabric material of a construction corresponding to that of said one of said first and second strips, with said additional strip being positioned so as to overlie said one of said first and second strips and so as to be adapted for engagement by said other of said strips at the free end of said inside strap, and said outside strap further mounts an additional strip of fabric material of a construction corresponding to that of said one of said third and fourth strips, with said additional strip of said outside strap being positioned so as to overlie said one of said third and fourth strips and so as to be adapted for engagement by said other of said third and fourth strips at said free end of said outside strap.

6. The ankle stabilizing appliance as defined in claim 1 wherein said interconnection means comprises a plurality of eyelet openings positioned along each of said front edges of said body member, and flexible lacing threaded through said eyelet openings.

7. The ankle stabilizing appliance as defined in claim 1 wherein said rear edge portion of said ankle portion is arcuately curved in an inward direction along its vertical length and so as to closely conform to the anatomy of the posterior portion of the wearer's foot.

8. An ankle stabilizing appliance adapted to provide protection against lateral ankle sprain during participation in sports activities, and comprising a boot-like body member of flexible material and adapted to receive the ankle and the rear foot portion of the wearer therein, said body member comprising an ankle portion adapted to overlie the sides and rear of the ankle of the wearer and having a length sufficient to extend above the malleoli of the wearer, a foot portion adapted to extend under the foot of the wearer, and with said ankle portion defining an inside panel on one side of the ankle, an outside panel on the other side of the ankle, and a rear edge portion which extends vertically between the inside and outside panels and thus along the Achilles tendon of the wearer, a pair of elongate non-elastic stabilizing straps, with said straps each having a first end fixed to said ankle portion at said rear edge portion thereof and at an elevation so as to be located above the malleoli of the wearer, and an opposite free end, and with said straps extending laterally in opposite directions and so as to define an inside strap extending from said rear edge portion toward said inside panel and an outside strap extending from said rear edge portion toward said outside panel, first releasable closure means for releasably interconnecting said inside panel of said ankle portion and said free end of said inside strap, and second releasable closure means for releasably interconnecting said outside panel of said ankle portion and said free end of said outside strap, a pair of binding straps, with said binding straps each having a first end fixed to said ankle portion at said rear edge portion thereof at an elevation corresponding to that of said stabilizing straps, and an opposite free end, and with said binding straps extending laterally in opposite directions and overlying said stabilizing straps, and pressure sensitive closure means attached to said free ends of said binding straps, whereby said inside strap may be brought across said inside panel of said ankle portion, over the top of the wearer's foot, downwardly across the outside of the wearer's foot, under the wearer's foot, and then upwardly and so that said free end thereof may be releasably attached to said first closure means, and whereby said outside strap may be brought across said outside panel of said ankle portion, over the top of the wearer's foot, downwardly across the inside of the wearer's foot, under the wearer's foot, and then upwardly so that said free end thereof may be releasably attached to said second closure means, and such that said binding straps are adapted to be looped about the ankle of the wearer and interconnected to each other and so as to overlie portions of said stabilizing straps.

9. The ankle stabilizing appliance as defined in claim 8 wherein said first releasable closure means comprises a first strip of fabric material composed of hook-like filaments and a second strip of fabric material composed of loop-like filaments, with one of said first and second strips being attached to said inside panel of said ankle portion and the other of said strips being attached to said free end of said inside strap, and said second releasable closure means comprises a third strip of fabric material composed of hook-like filaments and a fourth strip of fabric material composed of loop-like filaments, with one of said third and fourth strips being attached to the outside panel of said ankle portion and the other of said third and fourth strips being attached to said free end of said outside strap.

10. The ankle stabilizing appliance as defined in claim 9 wherein said inside strap further mounts an additional strip of fabric material of a construction corresponding to that of said one of said first and second strips, with said additional strip being positioned so as to overlie said one of said first and second strips and so as to be adapted for engagement by said other of said strips at the free end of said inside strap, and said outside strap further mounts an additional strip of fabric material of a construction corresponding to that of said one of said third and fourth strips, with said additional strip of said outside strap being positioned so as to overlie said one of said third and fourth strips and so as to be adapted for engagement by said other of said third and fourth strips at said free end of said outside strap.

* * * * *